(12) United States Patent
Ogura et al.

(10) Patent No.: US 9,336,918 B2
(45) Date of Patent: May 10, 2016

(54) SAMPLE-CONTAINING CELL FOR X-RAY MICROSCOPE AND METHOD FOR OBSERVING X-RAY MICROSCOPIC IMAGE

(75) Inventors: Toshihiko Ogura, Ibaraki (JP); Toru Takahashi, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 154 days.

(21) Appl. No.: 14/343,590

(22) PCT Filed: Aug. 31, 2012

(86) PCT No.: PCT/JP2012/005528
§ 371 (c)(1),
(2), (4) Date: Mar. 7, 2014

(87) PCT Pub. No.: WO2013/035292
PCT Pub. Date: Mar. 14, 2013

(65) Prior Publication Data
US 2014/0226797 A1 Aug. 14, 2014

(30) Foreign Application Priority Data
Sep. 9, 2011 (JP) .................................. 2011-197097

(51) Int. Cl.
*G21K 7/00* (2006.01)
*G21K 5/08* (2006.01)
(Continued)

(52) U.S. Cl.
CPC *G21K 5/08* (2013.01); *G01N 23/04* (2013.01); *G21K 7/00* (2013.01); *G01N 2223/309* (2013.01); *G01N 2223/612* (2013.01)

(58) Field of Classification Search
CPC ........... G21K 7/00; G21K 1/025; G21K 5/08; G01N 23/2251; H01J 35/14

USPC ..................... 378/43, 208, 119, 140, 161, 62; 250/368
See application file for complete search history.

(56) References Cited

U.S. PATENT DOCUMENTS

| | | | | |
|---|---|---|---|---|
| 5,107,526 A | * | 4/1992 | Hoover | G21K 7/00 378/210 |
| 5,216,699 A | * | 6/1993 | Iketaki | G21K 7/00 378/161 |

(Continued)

FOREIGN PATENT DOCUMENTS

| | | |
|---|---|---|
| JP | 2 138856 | 5/1990 |
| JP | 6 180400 | 6/1994 |

(Continued)

OTHER PUBLICATIONS

Extended European Search Report issued Apr. 16, 2015 in Patent Application No. 12830348.4.

(Continued)

*Primary Examiner* — David A Vanore
(74) *Attorney, Agent, or Firm* — Oblon, McClelland, Maier & Neustadt, L.L.P.

(57) ABSTRACT

Observation samples in a sample solution are held due to absorption or the like on a rear face of a first X-ray transmission film. In a mirror body, while an X-ray emission film and X-ray transmission films are bent to be convex outward due to a pressure difference, an X-ray transmission film is bent to be convex toward the X-ray transmission film side due to gas expansion in a second cavity part. This bending results in widening of a gap between the first and second X-ray transmission films in their center part more compared with a gap between their end parts. However, there is almost no change between the X-ray transmission films.

6 Claims, 5 Drawing Sheets

(51) Int. Cl.
*H01J 35/14* (2006.01)
*G01N 23/04* (2006.01)

(56) References Cited

U.S. PATENT DOCUMENTS

| | | | | |
|---|---|---|---|---|
| 5,528,646 A * | 6/1996 | Iketaki | ............ | G21K 7/00 378/43 |
| 5,550,378 A * | 8/1996 | Skillicorn | ............ | A61B 6/06 250/367 |
| 5,680,429 A | 10/1997 | Hirose et al. | | |
| 5,781,608 A * | 7/1998 | Tomie | ............ | H05G 2/001 378/119 |
| 5,832,052 A * | 11/1998 | Hirose | ............ | G21K 7/00 378/210 |
| 5,912,939 A * | 6/1999 | Hirsch | ............ | H05G 2/001 378/190 |
| 6,157,701 A | 12/2000 | Hirose et al. | | |
| 6,163,590 A * | 12/2000 | Wilkins | ............ | G21K 7/00 378/208 |
| 6,430,254 B2 * | 8/2002 | Wilkins | ............ | G21K 7/00 378/124 |
| 8,891,728 B2 * | 11/2014 | Ogura | ............ | G01N 23/2251 378/208 |
| 2001/0001010 A1 | 5/2001 | Wilkins | | |
| 2005/0207536 A1 * | 9/2005 | Shiraishi | ............ | G03F 7/70033 378/119 |
| 2012/0321037 A1 * | 12/2012 | Ogura | ............ | G01N 23/2251 378/43 |
| 2014/0226797 A1 * | 8/2014 | Ogura | ............ | G21K 7/00 378/208 |
| 2014/0362973 A1 * | 12/2014 | Ogura | ............ | H01J 35/08 378/62 |

FOREIGN PATENT DOCUMENTS

| | | |
|---|---|---|
| JP | 6-197097 A | 7/1994 |
| JP | 8 43600 | 2/1996 |
| JP | 8 194100 | 7/1996 |
| JP | 2001 519022 | 10/2001 |
| JP | 4565168 | 8/2010 |

OTHER PUBLICATIONS

Dachao Gao et al., "X-ray Ultramicroscopy Using Integrated Sample Cells", Optics Express, vol. 14, No. 17, XP055180846, Aug. 21, 2006, pp. 7889-7894.
International Search Report Issued Oct. 2, 2012 in PCT/JP12/005528 Filed Aug. 31, 2012.
Office Action issued Mar. 3, 2015 in Japanese Patent Application No. 2011-197097.

* cited by examiner

SAMPLE-CONTAINING CELL FOR X-RAY MICROSCOPE AND METHOD FOR OBSERVING X-RAY MICROSCOPIC IMAGE

TECHNICAL FIELD

The present invention relates to a technology for observing an X-ray microscopic image and particularly relates to a technology suitable for high-resolution X-ray microscope observation of a biological sample in a solution.

BACKGROUND ART

It is known that X-ray microscopes can perform high-resolution observation of a sample in a solution, giving a useful technique in the case where the observation target sample is a biological sample particularly. Particularly, on X-rays in a wavelength range of 2.3 to 4.4 nm (corresponding to an energy range of 284 to 540 eV) generally called "water window" (soft X-rays), differences in absorption coefficient between the constituent substances of the living body are large and the relevant X-rays, while transmitted without being absorbed by water, are liable to be absorbed by carbon and nitrogen, this leading to characteristics in which proteins and the like hardly allow the relevant X-rays to be transmitted. X-ray microscope observation using the soft X-rays is suitable for observing a biological sample.

The above-mentioned characteristics that the soft X-rays in the wavelength region of "water window" have enable an observation target object containing moisture (biological sample or sample in a solution) to be observed as it is, and in addition, enables observation in higher resolution than in the optical microscope observation because of the shorter wavelength than that of the visible light. Such reasons are promoting development of the microscope utilizing the X-rays in the "water window" wavelength region (soft X-ray microscope).

Notably, soft X-rays in a wavelength region of "carbon window" (5.0 to 4.5 nm) showing less absorption by carbon and soft X-rays in a region of a further shorter wavelength (0.6 to 2.3 nm) are also effective for observing a biological sample.

X-ray microscopes are categorized mainly into a scheme of irradiating the sample with an X-ray beam thinly focused using a light collecting system such as a zone plate (light collecting scheme) and a scheme of irradiating the sample with an X-ray beam from a point light source (point light source scheme).

The X-ray microscopes in the light collecting scheme are categorized into ones of irradiating transmission type and ones of scanning transmission type. The resolution depends on processing precision of the zone plate and the like and its theoretical limit is predicted to be approximately 10 to 15 nm.

On the other hand, the X-ray microscopes in the point light source scheme are categorized into a scheme of generating X-rays with a laser and a scheme of generating X-rays by means of irradiation with a charged particle beam such as an electron beam. There are proposed examples of the scheme of generating X-rays by means of irradiation with a charged particle beam, including a technique that an electron beam is allowed to incident on and through the surface of a sample supporting film to generate the X-rays in the sample supporting film and samples adhering to the rear face of the sample supporting film is irradiated with the X-rays (Patent Literature 1: Japanese Patent Laid-Open No. 8-43600; Patent Literature 2: Japanese Patent No. 4565168; Patent Literature 3: Japanese Patent Laid-Open No. 2-138856).

According to such a technique, exceedingly thinly focused charged particles can be allowed to be incident on the sample supporting film, suppressing a diffusion range of the charged particles to attain high resolution. Moreover, when a plurality of X-ray detectors are installed at various angles and positions below the sample supporting film (on its rear face side), inclined images depending on the installation angles can be obtained, affording as many inclined images as the number of the installed detectors in one charged particle beam scanning and also enabling a three-dimensional structure of the observation target sample to be reproduced based on these inclined images (Patent Literature 2).

As a sample supporting member (supporting film) used for such soft X-ray microscope observation, a silicon nitride film has been widely used. Since the silicon nitride film has excellent pressure resistance, it has been thought that even when the relevant silicon nitride film is provided in a window part of a sample-containing cell inside which is under atmospheric pressure, the usage of the sample-containing cell in the microscope apparatus inside which is under a vacuum suffers no difficulty at all. For example, according to the invention disclosed in Japanese Patent Laid-Open No. 6-180400 (Patent Literature 4), a sample cell in which two silicon nitride films are arranged opposite to each other with a predetermined interval is used, a recess for storing a sample solution is provided in the periphery of an X-ray transmission window, observation samples along with a solution are sealed between the silicon nitride films to be closed, and thus, X-ray microscope observation is performed.

CITATION LIST

Patent Literature

Patent Literature 1: Japanese Patent Laid-Open No. 8-43600
Patent Literature 2: Japanese Patent No. 4565168
Patent Literature 3: Japanese Patent Laid-Open No. 2-138856
Patent Literature 4: Japanese Patent Laid-Open No. 6-180400

SUMMARY OF INVENTION

Technical Problem

As mentioned above, since the silicon nitride film has excellent pressure resistance, it has been thought that the sample-containing cell using such a film as a sample supporting member (supporting film) practically suffers no difficulty at all in the usage inside the X-ray microscope apparatus. Nevertheless, the inventors consider that the sample-containing cell with the conventional configuration still leaves room for further improvement.

Figure 1A:
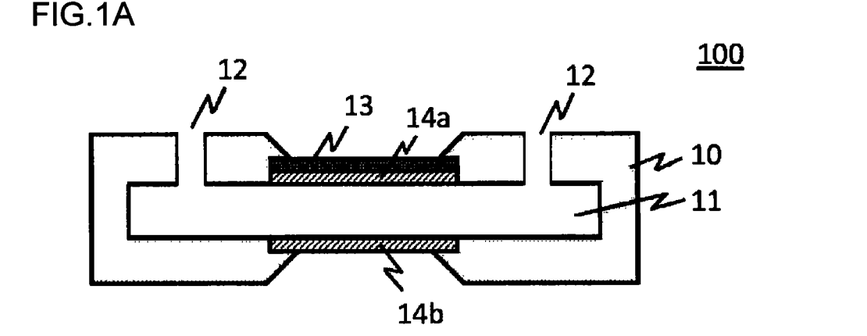
FIG. 1A is a diagram for explaining a problem arising in using a sample-containing cell with the conventional configuration in an X-ray microscope.
Figure 1B:
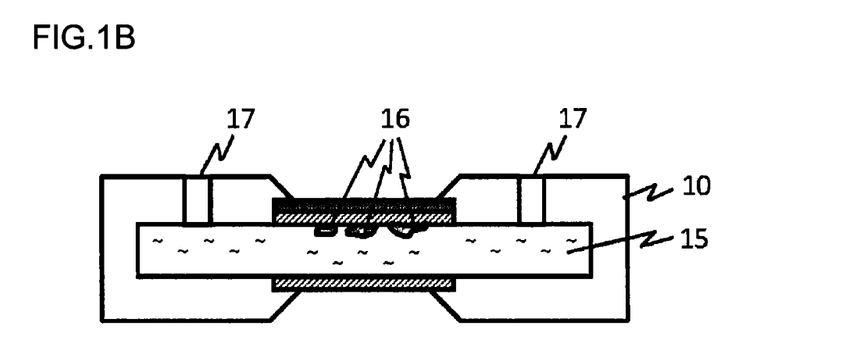
FIG. 1B is a diagram for explaining the problem arising in using a sample-containing cell with the conventional configuration in an X-ray microscope.
Figure 1C:
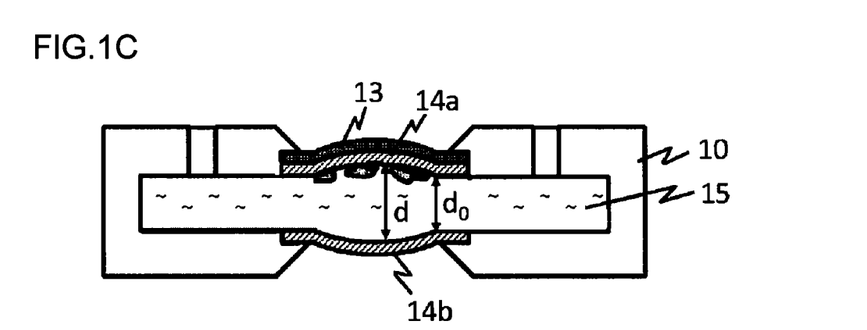
FIG. 1C is a diagram for explaining the problem arising in using a sample-containing cell with the conventional configuration in an X-ray microscope.

FIGS. 1A to C are diagrams for explaining a problem arising in using the sample-containing cell with the conventional configuration in an X-ray microscope. As illustrated in FIG. 1A, a sample-containing cell 100 includes a container part 10 having a cavity part 11 for containing observation samples along with a solution. Hole parts 12 through which a sample solution is introduced for filling are provided in the container part 10. In the center part of the container part 10, an X-ray emission film 13 that receives irradiation with charged particles and emits soft X-rays and a first X-ray transmission film 14a that transmits the soft X-rays and is capable of maintaining airtightness in the cavity part 11 are provided in this order in the upper portion of the figure. Similarly to the first X-ray transmission film 14a, a second X-ray transmission film 14b that transmits the soft X-rays from the X-ray emission film 13 and is capable of maintaining airtightness in the cavity part 11 is provided in the lower portion of the figure.

When such a sample-containing cell 100 is filled with a sample solution 15, observation samples 16 in the sample solution are held due to absorption or the like on the X-ray transmission film (on the rear face of the first X-ray transmission film 14a in the example illustrated in FIG. 1B). In other words, the X-ray transmission film also functions as a sample supporting film. After the filling with the sample solution, the hole parts 12 are closed with sealing members 17 and the sample-containing cell 100 is set inside the X-ray microscope.

In performing X-ray microscope observation, the inside of the mirror body is configured to be under a vacuum. In this stage, there arises the difference between the inner pressure of the sample-containing cell 100 and the pressure inside the mirror body of the X-ray microscope. The thicknesses of the X-ray emission film 13 and the X-ray transmission films 14a and 14b are small generally with a sub-micrometer level (for example, approximately 0.05 to 0.1 μm). Due to the pressure difference, the X-ray emission film 13 and the X-ray transmission films 14a and 14b are bent to be convex outward (FIG. 1C).

Occurrence of such bending results in widening of a gap d between the first X-ray transmission film 14a that also functions as a sample supporting film and the second X-ray transmission film 14b in the center part of these more compared with a gap $d_0$ between the end parts of these X-ray transmission films 14a and 14b. This means that an X-ray optical path length over the region which is significant for the X-ray microscope observation does not have uniformity, causing the following problem. Over the primary visual field region of the X-ray microscope observation, lengthening of the X-ray optical path length results in an increase in absorption of the X-rays by the sample solution 15 in accordance with the increase of the optical path length, causing sensitivity to deteriorate and image quality deterioration in observation image to arise.

An extent of the bending depends on the thicknesses and materials of the X-ray emission film 13 and the X-ray transmission films 14a and 14b and the gap $d_0$ being 5 μm under atmospheric pressure can sometimes become a gap d being 20 μm under a vacuum. There are thought examples of the cause for such a phenomenon, including that air bubbles generated due to the reduced pressure at any location in the sample solution 15, for example, lead to substantial increase in volume of the sample solution 15. In order to suppress this, it is thought that the sample solution 15, for example, is allowed to be at a reduced pressure for degassing in advance before the sample-containing cell 100 is set inside the X-ray microscope as an effective process. Nevertheless, such a process possibly causes exceeding evacuation in pressure inside the sample-containing cell 100. When the observation samples 16 are relatively vulnerable ones such as living body cells, their partial breakage or the like caused by this can disadvantageously affect the morphological observation of those as a result.

The present invention is devised in view of such problems regarding the sample-containing cell with the conventional configuration as mentioned above and an object is to provide a sample-containing cell contributing to high-resolution X-ray microscope observation of a biological sample in a solution particularly.

Solution to Problem

In order to solve the above-mentioned problems, there is provided a sample-containing cell according to a first aspect of the present invention, which is a sample-containing cell for an X-ray microscope, the sample-containing cell used in performing X-ray microscope observation in a vacuum mirror body, the sample-containing cell including: a cavity part for containing a sample solution inside; a charged particle incident window provided on one face of the sample-containing cell, for allowing charged particles to be incident on the cavity part; an X-ray emission film that receives irradiation with the charged particles and emits a characteristic X-ray in a soft X-ray region and a first X-ray transmission film that transmits the characteristic X-ray and also functions as an observation sample supporting film, the films provided in the charged particle incident window in this order; an X-ray transmission window provided on the other face of the sample-containing cell; and a second X-ray transmission film that transmits the characteristic X-ray, the film provided in the X-ray transmission window, wherein the cavity part is separated with a third X-ray transmission film that transmits the characteristic X-ray into a first cavity part on a side of the one face of the sample-containing cell and a second cavity part on a side of the other face of the sample-containing cell, and a hole part is provided in the sample-containing cell, for filling the first cavity part with the sample solution.

Moreover, there is provided a sample-containing cell according to a second aspect of the present invention, which is a sample-containing cell for an X-ray microscope, the sample-containing cell used in performing X-ray microscope observation in a vacuum mirror body, the sample-containing cell including: a cavity part for containing a sample solution inside; a charged particle incident window provided on one face of the sample-containing cell, for allowing charged particles to be incident on the cavity part; an X-ray emission film that receives irradiation with the charged particles and emits a characteristic X-ray in a soft X-ray region and a first X-ray transmission film that transmits the characteristic X-ray and also functions as an observation sample supporting film, the films provided in the charged particle incident window in this order; an X-ray transmission window provided on the other face of the sample-containing cell; and a second X-ray transmission film that transmits the characteristic X-ray, the film provided in the X-ray transmission window, wherein a hole part for filling the cavity part with the sample solution and a gas injection part for injecting gas into the cavity part are provided in the sample-containing cell.

Furthermore, there is provided a sample-containing cell according to a third aspect of the present invention, which is a sample-containing cell for an X-ray microscope, the sample-containing cell used in performing X-ray microscope observation in a vacuum mirror body, the sample-containing cell including: a sample introduction part equipped with a plunger operable therein for containing a sample solution inside; a charged particle incident window provided on one face of the sample-containing cell, for allowing charged particles to be incident on the sample introduction part; an X-ray emission film that receives irradiation with the charged particles and emits a characteristic X-ray in a soft X-ray region and a first X-ray transmission film that transmits the characteristic X-ray and also functions as an observation sample supporting film, the films provided in the charged particle incident window in this order; an X-ray transmission window provided on the other face of the sample-containing cell; and a second X-ray transmission film that transmits the characteristic X-ray, the film provided in the X-ray transmission window.

It is preferable for these sample-containing cells for an X-ray microscope to include a charged particle absorption film that transmits the characteristic X-ray and shields a charged particle beam, the film provided between the X-ray emission film and the first X-ray transmission film.

A method for observing an X-ray microscopic image according to the present invention is performed using the above-mentioned sample-containing cell according to the present invention.

Advantageous Effects of Invention

According to the present invention, even when the X-ray emission film and the X-ray transmission films are bent due to the pressure difference between the inside and outside at the interior of the mirror body, the X-ray optical path length in the sample solution does not lengthen and absorption of the X-rays by the sample solution can be suppressed. Thereby, a biological sample in a solution can undergo high-resolution X-ray microscope observation.

DESCRIPTION OF EMBODIMENTS

Hereinafter, a sample-containing cell for an X-ray microscope and a method for observing an X-ray microscopic image using the same according to the present invention will be described with reference to the drawings.

As mentioned above, in the sample-containing cell with the conventional structure, the X-ray emission film and the X-ray transmission films are bent to be convex outward due to the pressure difference between the inside and outside at the interior of the mirror body of the X-ray microscope under a vacuum. The X-ray optical path length over the primary visual field region of the X-ray microscope observation lengthens, this causing the X-rays to be absorbed by the sample solution and image quality deterioration in observation image to arise.

The present invention is to solve the problem as follows. A sample solution containing part and a gas containing part in a cavity part for containing a sample solution are provided inside the sample-containing cell. An increase in X-ray optical path length due to the pressure difference between the inside and outside is imposed on the above-mentioned gas containing part that does not give X-ray absorption. Thus, increase of the X-ray optical path length in the sample solution containing part is suppressed.

Moreover, the problem is to be solved using a sample-containing cell according to another embodiment as follows. A gas bubble (air bubble) is introduced into the sample solution contained in the cavity part, an increase in X-ray optical path length due to the pressure difference between the inside and outside is imposed on the above-mentioned air bubble that does not give X-ray absorption, this enabling increase of the X-ray optical path length in the sample solution to be suppressed.

In other words, in the sample-containing cell according to the present invention, even when the X-ray emission film and the X-ray transmission films are bent due to the pressure difference between the inside and outside at the interior of the mirror body, lengthening of the X-ray optical path length takes place in the gas portion that does not give X-ray absorption. Thus, absorption of the X-rays by the sample solution can be suppressed, this leading to no image quality deterioration in observation image.

Figure 2A:
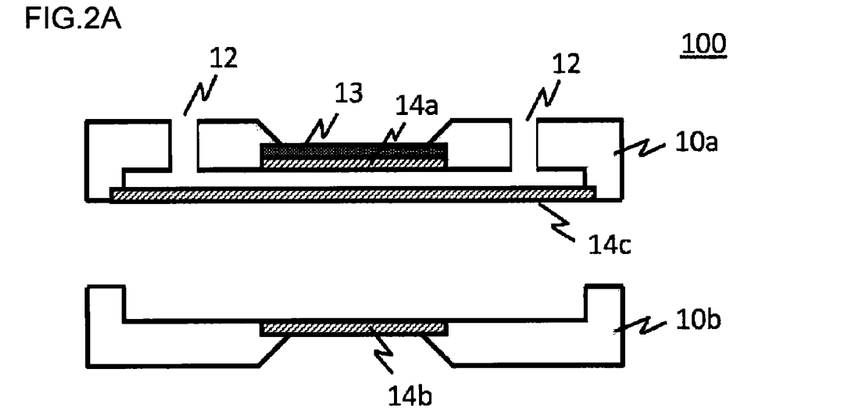
FIG. 2A is a schematic cross-sectional view for explaining a basic configuration of a sample-containing cell according to a first embodiment of the present invention.
Figure 2B:
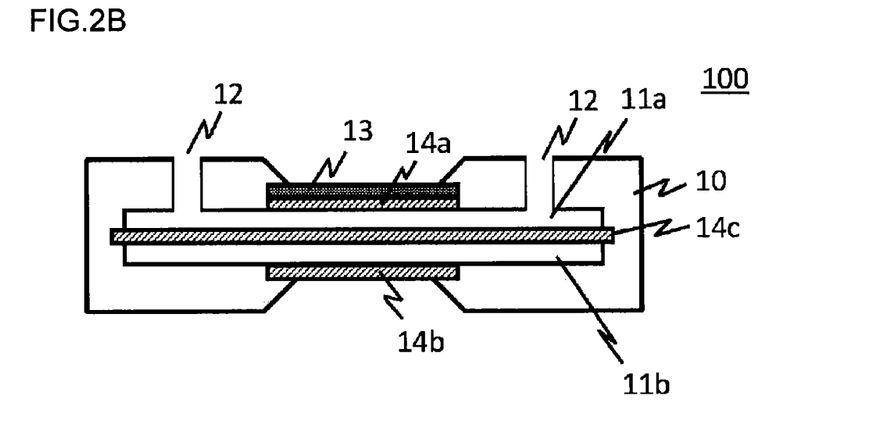
FIG. 2B is a schematic cross-sectional view for explaining the basic configuration of the sample-containing cell according to the first embodiment of the present invention.
Figure 2C:
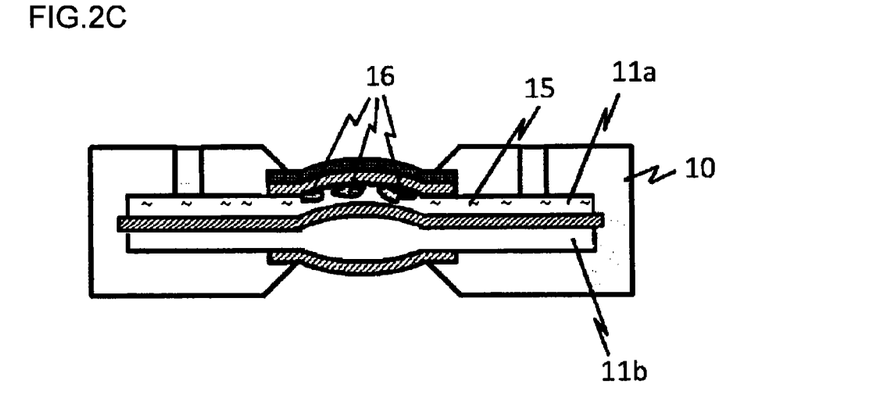
FIG. 2C is a schematic cross-sectional view for explaining the basic configuration of the sample-containing cell according to the first embodiment of the present invention.

FIGS. 2A to C are schematic cross-sectional views for explaining a basic configuration of a sample-containing cell according to a first embodiment of the present invention. In FIG. 2A, a container part 10 of a sample-containing cell 100 is configured to be separable into an upper part 10a and a lower part 10b, whereas it may be integrated into one (FIG. 2B).

In the sample-containing cell 100, a sample solution is contained in a cavity part 11 which is to be formed inside the container part 10. A charged particle incident window for allowing charged particles to be incident on the cavity part is provided on one face of the sample-containing cell 100. In this charged particle incident window, an X-ray emission film 13 that receives irradiation with the charged particles and emits characteristic X-rays in the soft X-ray region and a first X-ray transmission film 14a that transmits the characteristic X-rays and also functions as an observation sample supporting film are provided in this order.

A window for transmitting X-rays emitted from the inside of the cavity part 11 and enabling observation from the outside (X-ray transmission window) is provided on the other face of the sample-containing cell 100. In the X-ray transmission window, a second X-ray transmission film 14b that transmits the above-mentioned characteristic X-rays is provided.

A third X-ray transmission film 14c that transmits the above-mentioned characteristic X-rays is provided on the lower side of the upper part 10a of the container part 10. In the state where the upper part 10a of the container part and the lower part 10b of the container part are coupled together, a cavity part on the upper part 10a side of the container part (first cavity part 11a) is sealed with the third X-ray transmission film 14c and the first X-ray transmission film 14a, and a cavity part on the lower part 10b side of the container part (second cavity part 11b) is sealed with the third X-ray transmission film 14c and the second X-ray transmission film 14b.

In other words, the cavity part 11 is separated with the third X-ray transmission film 14c into the first cavity part 11a on the one face side of the sample-containing cell 100 and the second cavity part 11b on the other face side thereof. The first cavity part 11a is filled with a sample solution through a hole part 12.

Observation samples 16 in a sample solution 15 are held due to absorption or the like on the rear face of the first X-ray transmission film 14a. After the filling with the sample solution 15, the hole parts 12 are closed with sealing members 17 and the sample-containing cell 100 is set inside the X-ray microscope. Notably, as a result, the second cavity part 11b is filled with gas in the environment of introducing the observation samples for the filling (generally air).

After setting the sample-containing cell 100, the X-ray emission film 13 and the X-ray transmission films 14a and 14b are bent due to the pressure difference to be convex outward as mentioned above, and in this stage, the X-ray transmission film 14c is bent due to gas expansion in the second cavity part 11b to be convex toward the X-ray transmission film 14a side (FIG. 2C).

Occurrence of such bending results in widening of a gap between the first X-ray transmission film 14a that also functions as a sample supporting film and the second X-ray transmission film 14b in the center part of these more compared with a gap between the end parts of these X-ray transmission films 14a and 14b. However, over the primary visual field region of the X-ray microscope observation, despite the fact that an X-ray optical path length between the X-ray transmission films 14b and 14c lengthens, the relevant optical path length between the X-ray transmission films 14a and 14c suffers almost no change.

Accordingly, even when the X-ray emission film and the X-ray transmission films are bent due to the pressure difference between the inside and outside at the interior of the mirror body, lengthening of the X-ray optical path length arises in the second cavity part 11b (gas portion) with no occurrence of X-ray absorption, and absorption of the X-rays by the sample solution 15 is suppressed.

FIGS. 3A to D are schematic cross-sectional views for explaining a basic configuration of a sample-containing cell according to a second embodiment of the present invention.

Figure 3A:
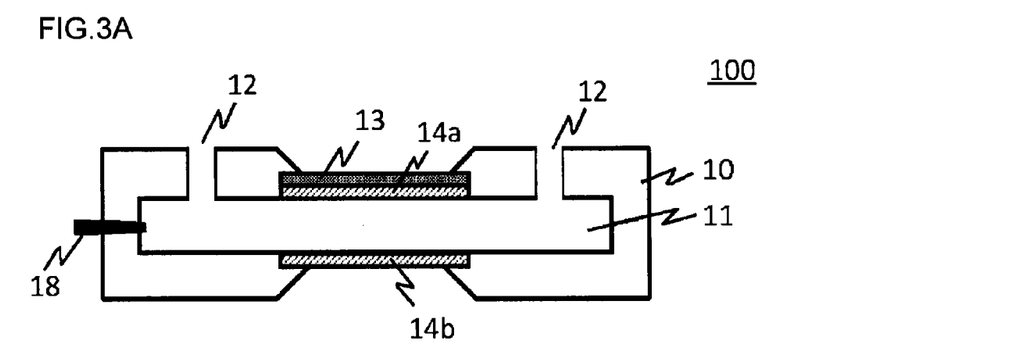
FIG. 3A is a schematic cross-sectional view for explaining a basic configuration of a sample-containing cell according to a second embodiment of the present invention.

In the sample-containing cell 100, a sample solution is contained in the cavity part 11 which is to be formed inside the container part 10. The charged particle incident window for allowing charged particles to be incident on the cavity part is provided on one face of the sample-containing cell 100. In this charged particle incident window, the X-ray emission film 13 that receives irradiation with the charged particles and emits characteristic X-rays in the soft X-ray region and the first X-ray transmission film 14a that transmits the characteristic X-rays and also functions as an observation sample supporting film are provided in this order.

A window for transmitting X-rays emitted from the inside of the cavity part 11 and enabling observation from the outside (X-ray transmission window) is provided on the other face of the sample-containing cell 100. In the X-ray transmission window, a second X-ray transmission film 14b that transmits the above-mentioned characteristic X-rays is provided.

Figure 3B:
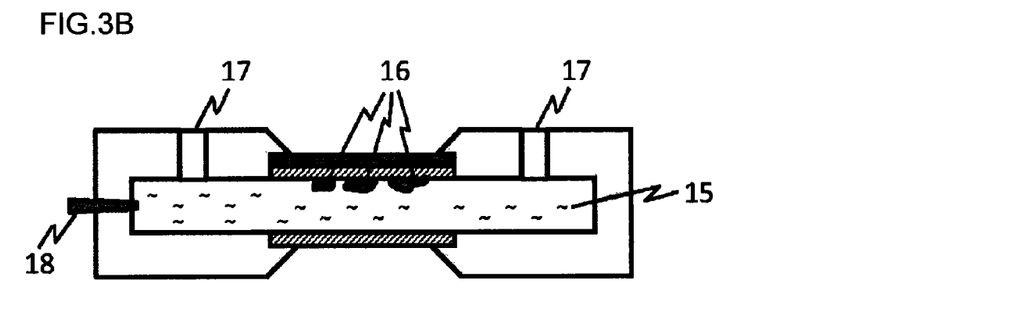
FIG. 3B is a schematic cross-sectional view for explaining the basic configuration of the sample-containing cell according to the second embodiment of the present invention.
Figure 3C:
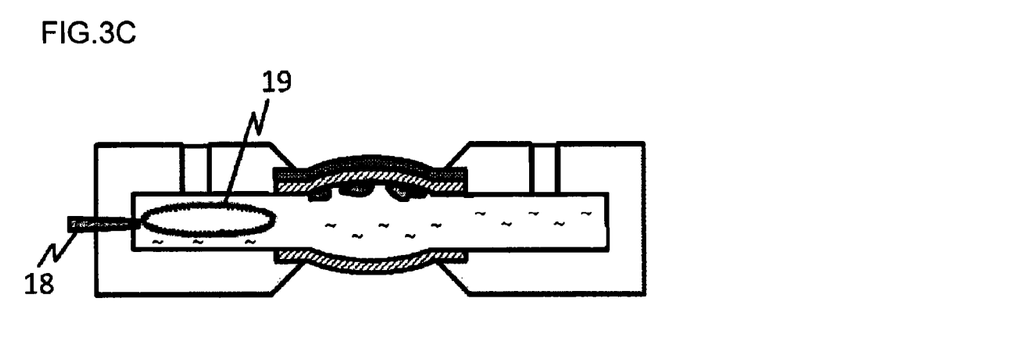
FIG. 3C is a schematic cross-sectional view for explaining the basic configuration of the sample-containing cell according to the second embodiment of the present invention.

The cavity part 11 is filled with the sample solution 15 through the hole part 12. The observation samples 16 in the sample solution 15 are held due to absorption or the like on the rear face of the first X-ray transmission film 14a. After the filling with the sample solution 15, the hole parts 12 are closed with the sealing members 17 and the sample-containing cell 100 is set inside the X-ray microscope.

A gas injection part 18 for injecting gas into the cavity part 11 is provided in the sample-containing cell 100.

Figure 3D:
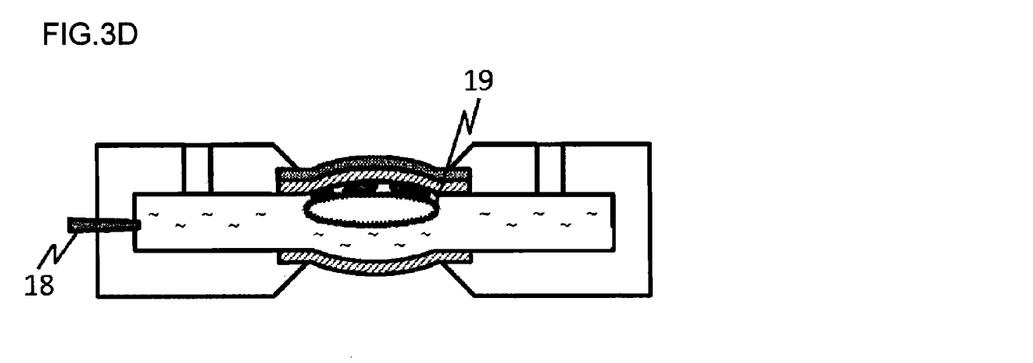
FIG. 3D is a schematic cross-sectional view for explaining the basic configuration of the sample-containing cell according to the second embodiment of the present invention.

When the sample-containing cell 100 is set, as mentioned above, the X-ray emission film 13 and the X-ray transmission films 14a and 14b are bent to be convex outward due to the pressure difference. Gas is injected into the cavity part 11 through the gas injection part 18 (FIG. 3C) and this gas bubble 19 is introduced between the X-ray transmission films 14a and 14b (FIG. 3D).

Occurrence of the bending of the X-ray emission film 13 and the X-ray transmission films 14a and 14b results in widening of a gap between the first X-ray transmission film 14a that also functions as a sample supporting film and the second X-ray transmission film 14b in the center part of these more compared with a gap between the end parts of these X-ray transmission films 14a and 14b. However, when an increase in X-ray optical path length over the primary visual field region of the X-ray microscope observation is made equal to a thickness of the gas bubble 19 by controlling the injection gas amount, absorption of the X-rays by the sample solution 15 is suppressed.

Examples of the above-mentioned injection gas can include, for example, air, helium and the like. Supposing that the energy of the X-rays is 300 eV, the thickness at which the strength attenuates to 1/e is approximately 1.5 mm for air and approximately 10 mm for helium compared with that for water being approximately 2.3 μm.

Notably, taking account of movability of the gas bubble 19 in the cavity part 11, it is preferable for a gap between the first X-ray transmission film and the second X-ray transmission film in the state where these films are bent under a vacuum to be 0.1 to 0.5 mm in the case of the gas being air, and moreover, to be 0.1 to 5 mm in the case of the gas being helium, still preferably 0.1 to 1 mm.

Examples of the method for injecting the gas include a method of introducing the gas into the cavity part 11, taking advantage of the reduced pressure in the cell arising from the pressure difference between the inside and outside caused in the mirror body, and a method of injecting the gas by means of compression from the outside of the cell 100.

Since the expansion rate of liquid according to pressure is small compared with gas by nature, the expansion amount under a vacuum is small. Therefore, the interior of the cell is allowed to be under a reduced pressure. Since the state of the reduced pressure is a harsh environment for the samples such as living body cells, the state of too much reduced pressure should be prevented. Specifically, it is not desirable for the inner pressure of the cell to be ½ atm or less. Assuming that a volume expansion amount of the cavity part in the cell due to the reduced pressure is 1, the inner pressure of the cell can be made approximately ½ atm when gas of 2 in volume is injected into the cavity part.

Notably, the sample-containing cell with the structure illustrated in FIGS. 3A to D is also effective to be used as follows.

Figure 4A:
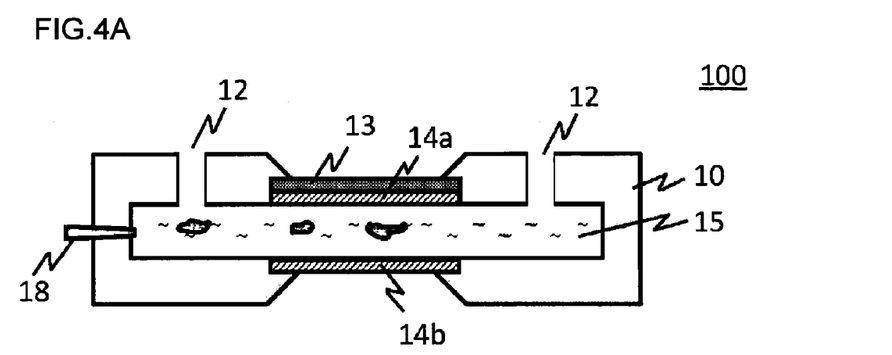
FIG. 4A is a diagram for explaining one example of a method for utilizing the sample-containing cell with the structure illustrated in FIGS. 3A to D.
Figure 4B:
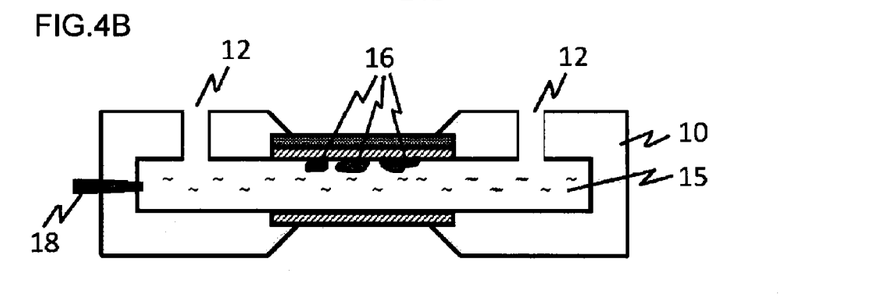
FIG. 4B is a diagram for explaining one example of the method for utilizing the sample-containing cell with the structure illustrated in FIGS. 3A to D.
Figure 4C:
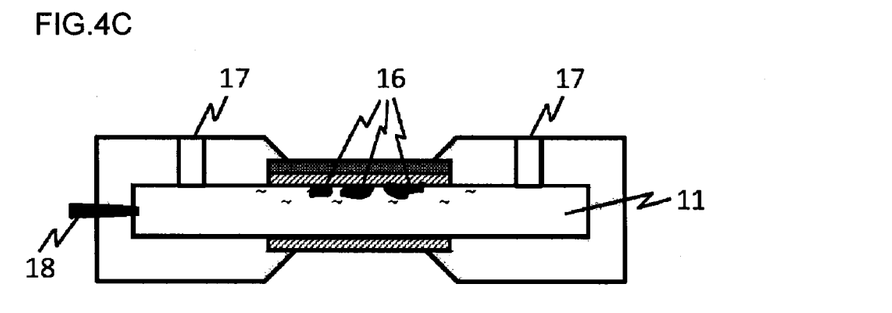
FIG. 4C is a diagram for explaining one example of the method for utilizing the sample-containing cell with the structure illustrated in FIGS. 3A to D.

FIGS. 4A to D are diagrams for explaining one example of a method for utilizing the sample-containing cell with the structure illustrated in FIGS. 3A to D. Once, the cavity part 11 is filled with the sample solution 15 (FIG. 4A) and the observation samples 16 are held due to absorption or the like utilizing surface tension or the like on first X-ray transmission film 14a (FIG. 4B). After that, the sample solution 15 is discharged from the cavity part 11 to the outside and the hole parts 12 are closed with the sealing members 17 to set the sample-containing cell 100 inside the X-ray microscope (FIG. 4C).

Figure 4D:
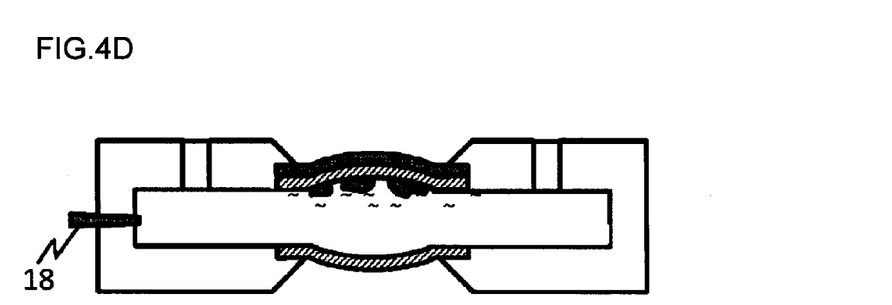
FIG. 4D is a diagram for explaining one example of the method for utilizing the sample-containing cell with the structure illustrated in FIGS. 3A to D.

When setting the sample-containing cell, as mentioned above, the X-ray emission film 13 and the X-ray transmission films 14a and 14b are bent to be convex outward due to the pressure difference. Since the sample solution (solution) in the cavity part 11 is just little in amount remaining on the surface of the observation samples 16, absorption of the X-rays by the sample solution 15 does not take place to an extent to which the microscope observation is disadvantageously affected (FIG. 4D).

The sample-containing cell according to the present invention can be represented by various embodiments other than the above-mentioned configurations. For example, a configuration is supposed in which a charged particle absorption film that transmits the characteristic X-rays and shields the charged particle beam is included between the X-ray emission film 13 and the first X-ray transmission film 14a, this preferably enabling damage on the observation samples due to irradiation with the charged particle beam to be reduced.

Moreover, when the observation samples are allowed to be supported on the first X-ray transmission film, there can be various techniques other than the embodiment according to which surface tension is utilized. For example, a very thin absorption film may be provided on the sample supporting surface of the first X-ray transmission film or the observation samples may be absorbed by means of electrostatic action due to voltage application.

When the gas bubble is injected into the cavity part, for example, a sensor, which is provided in the vicinity of the X-ray transmission window, may take a technique such as capacitance measurement and electric resistivity measurement to calculate a suitable injection gas amount or may take a technique, for example, in which the injection gas amount is regulated by means of remote manipulation, observing the status of the cell inside the mirror body, other than the embodiment according to which gas with a calculated amount based on a beforehand expected expansion amount is injected.

Figure 5:
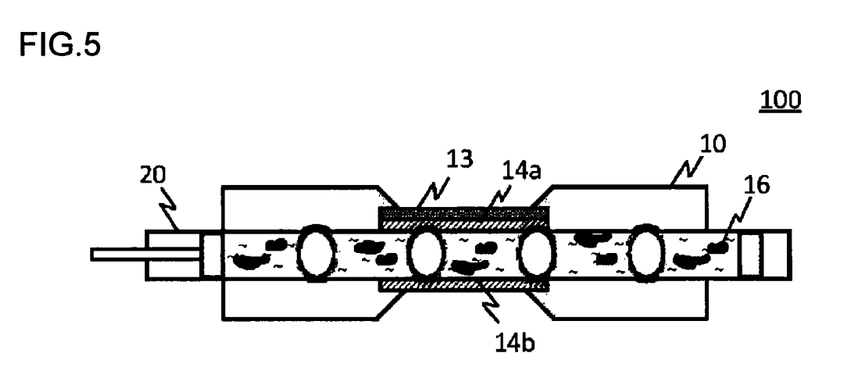
FIG. 5 is a schematic cross-sectional view for explaining a basic configuration of a sample-containing cell according to a third embodiment of the present invention.

Furthermore, as illustrated in FIG. 5, a long sample introduction tube 20 in the cell is used equipped with a plunger operable therein. The inside of the sample introduction tube 20 is filled with gas A (for example, oxygen gas); a sample solution a (for example, solvent liquid); gas B (for example, carbon dioxide gas); a sample solution b (for example, protein solution); gas C (for example, argon gas); a sample solution c (for example, antibody solution); gas D (for example, helium gas); a sample solution d (for example, chemical liquid), for example, wherein different kinds of gas and solutions are beforehand introduced for the filling, these being partitioned from one another. In observation, these may be sequentially moved to be observed under different conditions. Although only a part of the sample introduction tube 20 is illustrated in the figure, a sufficiently long plunger is configured in reality. The design is made such that the above-mentioned movement of the gas portions and the sample solution portions can be performed with no difficulty.

Notably, since there sometimes is a case where a reduced pressure causes bubbles in a solution with dissolved gas, it is still preferable for the solution to be degassed under a reduced pressure beforehand to be used. Herein, it is desirable for the pressure in the degassing under a reduced pressure to be a lower value than in the usage conditions, specifically ⅔ atm or less, or effective to be a further lower pressure such as approximately 0.1 atm depending on the observation object.

Such a method for introducing samples in a single channel manner has a merit that the sample-containing cell that once has been set is not needed to be taken outside the mirror body, this enabling the observations under various different kinds of conditions to be performed in a short time. Examples of the movement of the sample solution portions and the gas portions can include, for example, known techniques of a valve of a pressurized air chamber operable by ON/OFF switching and an electromagnetic vibratory micro pump.

INDUSTRIAL APPLICABILITY

According to the present invention, a biological sample in a solution can undergo high-resolution X-ray microscope observation.

REFERENCE SIGNS LIST

100 Sample-containing cell
10 Container part
10a Upper part
10b Lower part
11 Cavity part
11a First cavity part
11b Second cavity part
12 Hole part
13 X-ray emission film
14a First X-ray transmission film
14b Second X-ray transmission film
14c Third X-ray transmission film
15 Sample solution
16 Observation sample
17 Sealing member
18 Gas injection part
19 Gas bubble
20 Sample introduction tube

The invention claimed is:

1. A sample-containing cell for an X-ray microscope, the sample-containing cell used in performing X-ray microscope observation in a vacuum mirror body, the sample-containing cell comprising:
   a cavity part for containing a sample solution inside;
   a charged particle incident window provided on one face of the sample-containing cell, for allowing charged particles to be incident on the cavity part;
   an X-ray emission film that receives irradiation with the charged particles and emits a characteristic X-ray in a soft X-ray region and a first X-ray transmission film that transmits the characteristic X-ray and also functions as an observation sample supporting film, the films provided in the charged particle incident window in this order;
   an X-ray transmission window provided on the other face of the sample-containing cell; and
   a second X-ray transmission film that transmits the characteristic X-ray, the film provided in the X-ray transmission window, wherein
   the cavity part is separated with a third X-ray transmission film that transmits the characteristic X-ray into a first cavity part on a side of the one face of the sample-containing cell and a second cavity part on a side of the other face of the sample-containing cell, and
   a hole part is provided in the sample-containing cell, for filling the first cavity part with the sample solution.

2. The sample-containing cell for an X-ray microscope according to claim 1, further comprising:
a charged particle absorption film that transmits the characteristic X-ray and shields a charged particle beam, the film provided between the X-ray emission film and the first X-ray transmission film.

3. A sample-containing cell for an X-ray microscope, the sample-containing cell used in performing X-ray microscope observation in a vacuum mirror body, the sample-containing cell comprising:
a cavity part for containing a sample solution inside;
a charged particle incident window provided on one face of the sample-containing cell, for allowing charged particles to be incident on the cavity part;
an X-ray emission film that receives irradiation with the charged particles and emits a characteristic X-ray in a soft X-ray region and a first X-ray transmission film that transmits the characteristic X-ray and also functions as an observation sample supporting film, the films provided in the charged particle incident window in this order;
an X-ray transmission window provided on the other face of the sample-containing cell; and
a second X-ray transmission film that transmits the characteristic X-ray, the film provided in the X-ray transmission window, wherein
a hole part for filling the cavity part with the sample solution and a gas injection part for injecting gas into the cavity part are provided in the sample-containing cell.

4. The sample-containing cell for an X-ray microscope according to claim 3, further comprising:
a charged particle absorption film that transmits the characteristic X-ray and shields a charged particle beam, the film provided between the X-ray emission film and the first X-ray transmission film.

5. A sample-containing cell for an X-ray microscope, the sample-containing cell used in performing X-ray microscope observation in a vacuum mirror body, the sample-containing cell comprising:
a sample introduction part equipped with a plunger operable therein for containing a sample solution inside;
a charged particle incident window provided on one face of the sample-containing cell, for allowing charged particles to be incident on the sample introduction part;
an X-ray emission film that receives irradiation with the charged particles and emits a characteristic X-ray in a soft X-ray region and a first X-ray transmission film that transmits the characteristic X-ray and also functions as an observation sample supporting film, the films provided in the charged particle incident window in this order;
an X-ray transmission window provided on the other face of the sample-containing cell; and
a second X-ray transmission film that transmits the characteristic X-ray, the film provided in the X-ray transmission window.

6. The sample-containing cell for an X-ray microscope according to claim 5, further comprising:
a charged particle absorption film that transmits the characteristic X-ray and shields a charged particle beam, the film provided between the X-ray emission film and the first X-ray transmission film.

* * * * *